US008303909B2

(12) United States Patent
Friske

(10) Patent No.: US 8,303,909 B2
(45) Date of Patent: Nov. 6, 2012

(54) MICROFLUIDIC ASSEMBLY

(75) Inventor: Mark Stephen Friske, Campbell, NY (US)

(73) Assignee: Corning Incorporated, Corning, NY (US)

( * ) Notice: Subject to any disclaimer, the term of this patent is extended or adjusted under 35 U.S.C. 154(b) by 154 days.

(21) Appl. No.: 12/710,924

(22) Filed: Feb. 23, 2010

(65) Prior Publication Data

US 2011/0129395 A1 Jun. 2, 2011

Related U.S. Application Data

(60) Provisional application No. 61/265,186, filed on Nov. 30, 2009.

(51) Int. Cl.

| | |
|---|---|
| ***G01N 15/06*** | (2006.01) |
| ***G01N 33/00*** | (2006.01) |
| ***G01N 33/48*** | (2006.01) |

(52) U.S. Cl. ........... 422/503; 422/50; 422/68.1; 422/81; 422/82; 422/502; 422/509; 436/43; 436/174; 436/180

(58) Field of Classification Search .................... 422/50, 422/68.1, 81, 82, 502, 503, 504, 509; 436/43, 436/174, 180

See application file for complete search history.

(56) References Cited

U.S. PATENT DOCUMENTS

| | | | | |
|---|---|---|---|---|
| 6,832,787 | B1 | 12/2004 | Renzi | 285/124.1 |
| 7,569,127 | B1 | 8/2009 | Cho | |
| 2002/0124896 | A1 | 9/2002 | O'Connor et al. | |
| 2009/0162265 | A1 * | 6/2009 | Poissy et al. | 422/200 |
| 2010/0196212 | A1 * | 8/2010 | Reed et al. | 422/100 |
| 2010/0200402 | A1 * | 8/2010 | Li et al. | 204/451 |

FOREIGN PATENT DOCUMENTS

| | | | |
|---|---|---|---|
| EP | 1352686 | A1 | 10/2003 |
| WO | 01/70400 | | 9/2001 |
| WO | WO02/070942 | A1 | 9/2002 |
| WO | 2004/034028 | | 4/2004 |
| WO | WO2007/073281 | A1 | 6/2007 |

* cited by examiner

*Primary Examiner* — Brian J Sines

(74) *Attorney, Agent, or Firm* — Gregory V. Bean

(57) ABSTRACT

Embodiments of a microfluidic assembly comprise at least two adjacent microstructures and a plurality of interconnecting fluid conduits which connect an outlet port of one microstructure to an inlet port of an adjacent microstructure. Each microstructure comprises an inlet flow path and an outlet flow path not aligned along a common axis. Moreover, the microfluidic assembly defines a microfluidic assembly axis along which respective inlet ports of adjacent microstructures are oriented or alternatively along which respective outlet ports of adjacent microstructures are oriented, and each microstructure is oriented relative to the microfluidic assembly axis at a nonorthogonal angle.

19 Claims, 4 Drawing Sheets

MICROFLUIDIC ASSEMBLY

PRIORITY

This application claims priority to U.S. Provisional Patent Application No. 61/265,186, filed Nov. 30, 2009, titled “Microfluidic Assembly”.

BACKGROUND

The present disclosure is generally directed to microfluidic devices, and, more specifically, to microfluidic devices configured to reduce pressure drop of fluid reactants flowing therein.

SUMMARY

Microfluidic assemblies are devices comprising microreactors, which may also be referred to as microchannel reactors. A microreactor is a device in which a moving or static sample is confined and subject to processing. In some cases, the processing involves the analysis of chemical reactions. In others, the processing is executed as part of a manufacturing process utilizing two distinct reactants. In still others, a moving or static sample is confined in a microreactor as heat is exchanged between the sample and an associated heat exchange fluid. Such processes may also be combined in a single microreactor. In any case, the microreactors are defined according to the dimensions of their channels, which are generally on the order of from 0.1 to 5 mm, desirably from 0.5 to 2 mm. Microchannels are the most typical form of such confinement and the microreactor is usually a continuous flow reactor, as opposed to a batch reactor. The reduced internal dimensions of the microchannels provide considerable improvement in mass and heat transfer rates. In addition, microreactors offer many advantages over conventional scale reactors, including vast improvements in energy efficiency, reaction speed, reaction yield, safety, reliability, scalability, etc.

Microfluidic assembly, which may also be referred to as microstructure assemblies, may comprise a plurality of distinct fluidic microstructures that are in fluid communication with each other and are configured to execute different functions in the microreactor. For example, and not by way of limitation, an initial microstructure may be configured to mix two reactants. Subsequent microstructures may be configured for heat exchange, quenching, hydrolysis, etc, or simply to provide a controlled residence time for the mixed reactants. The various distinct microstructures must often be placed in serial or parallel fluid communication with each other. In many cases, the associated components for directing the reactants to the proper microstructures within the network can be fairly complex. Further, the components need to be configured for operation under high temperatures and pressures. Microfluidic assemblies employ a variety of fluidic ducts, fittings, adapters, O-rings, screws, clamps, and other types of connection elements to interconnect various microstructures within the microreactor configuration.

The method by which microstructures are assembled into a microfluidic assembly may impact the pressure drop, the complexity of the assembly, the complexity of the components that must be used to produce the assembled reactor, and the stress experienced by the component parts during use. Conventional microstructures and connections may be designed such that the connections for the inlet and outlet of the reactant fluid are on the same axis relative to the microstructure; however, this aligned structure requires deviations from a straight fluid flow path (e.g., bends, turns, curves the microchannels) in order to align the outlet port with the inlet port. These deviations are a major source of back pressure and pressure drop variability in microstructures.

According to one embodiment of the present disclosure, a microfluidic assembly is provided. The microfluidic assembly comprises at least two adjacent microstructures and a plurality of interconnecting fluid conduits, wherein each microstructure comprises at least one inlet port disposed on an inlet side of the microstructure and at least one outlet port disposed on an outlet side of the microstructure opposite the inlet side of the microstructure. The inlet port defines an inlet flow path, the outlet port defines an outlet flow path, and the inlet flow path and the outlet flow path are not aligned along a common axis. Respective interconnecting fluid conduits connect an outlet port of one microstructure to an inlet port of an adjacent microstructure. Moreover, each microstructure comprises an internal planar flow path in fluid communication with the inlet port and the outlet port. The microfluidic assembly defines a microstructure assembly axis along which respective inlet ports of adjacent microstructures are oriented or alternatively along which respective outlet ports of adjacent microstructures are oriented. Furthermore, each microstructure is oriented relative to the microfluidic assembly axis at a nonorthogonal angle.

These and additional features provided by the embodiments of the present disclosure will be more fully understood in view of the following detailed description, in conjunction with the drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
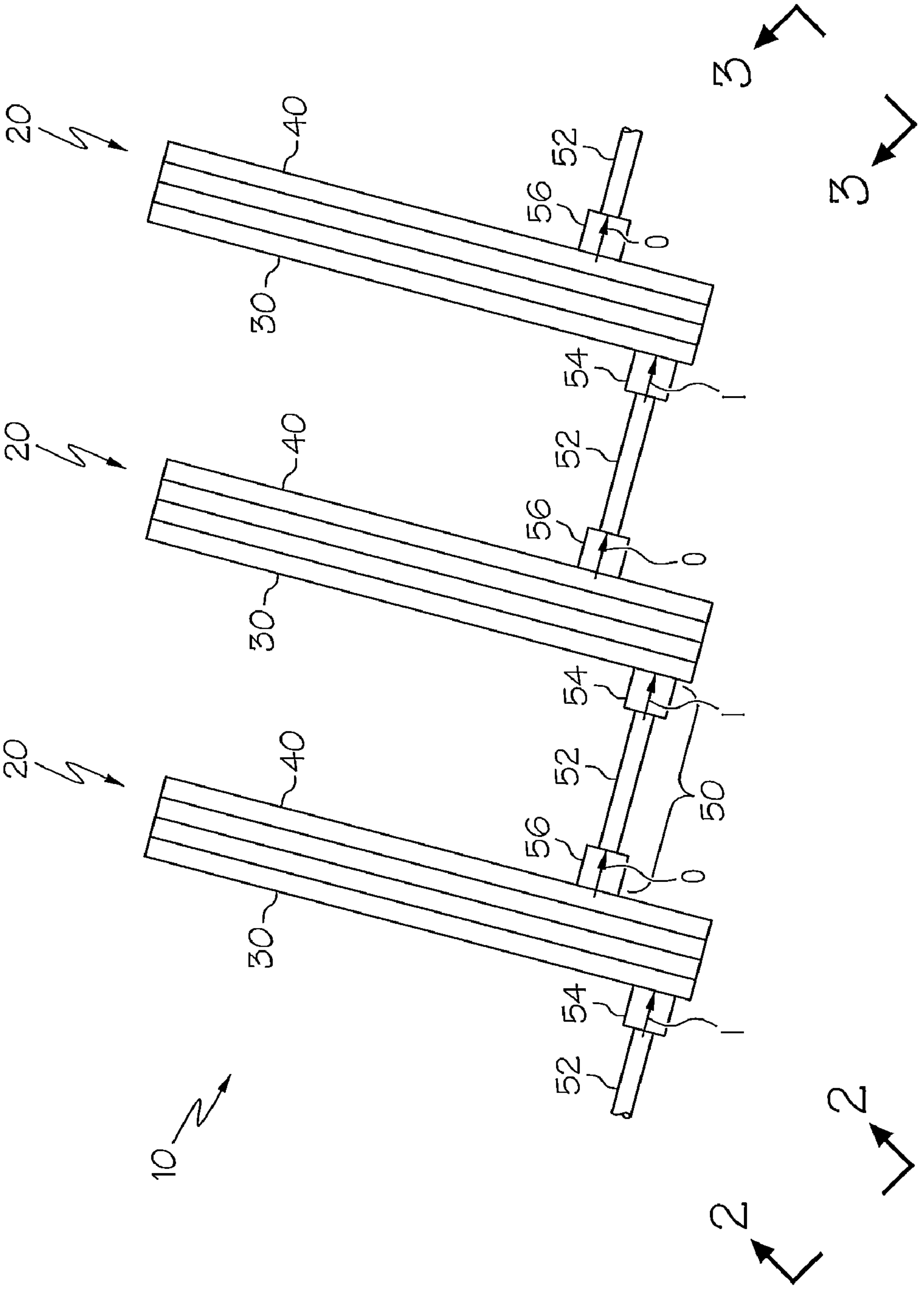
FIG. 1 is a top view of a microfluidic assembly according to one or more embodiments of the present disclosure.

The embodiments set forth in the drawings are illustrative in nature and not intended to be limiting of the invention defined by the claims. Moreover, individual features of the drawings and the claims will be more fully apparent and understood in view of the detailed description.

DETAILED DESCRIPTION

Referring to FIGS. 1-4, the microfluidic assembly 10 comprises at least two adjacent microstructures 20 coupled by at least one interconnecting fluid conduit 50. As used herein, a microfluidic 10 assembly refers to a plurality of coupled microstructures 20, and each microstructure 20 is defined as a comprising a plurality of microchannels having dimensions in the order of about 0.1 to 5 mm. Although the figures only depict 2 or 3 microstructures 20 in a microfluidic assembly 10, it is contemplated that any number of microstructures 20 may be used in the microfluidic assembly 10. As shown in detail below, the adjacent microstructures 20 are disposed parallel to each other, but on a diagonal relative to the microfluidic assembly axis M. This allows connection of microstructures without requiring the inlet port 32 and the outlet port 42 of an individual microstructure 20 to be aligned on the same axis, and thereby reduces pressure drops in the microreactors 20 specifically and the microfluidic assembly 10 generally.

Figure 2:
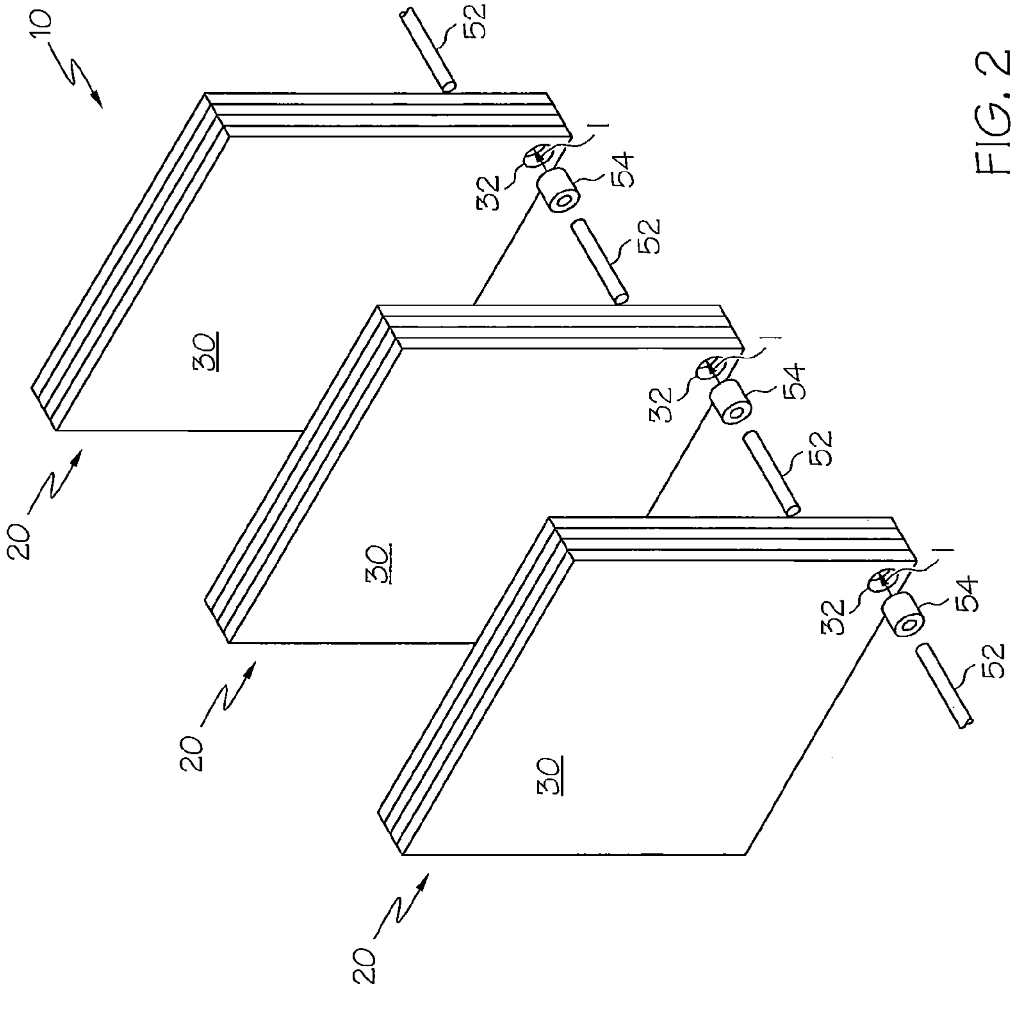
FIG. 2 is an exploded perspective view depicting the microfluidic assembly from the inlet side according to one or more embodiments of the present disclosure.
Figure 3:
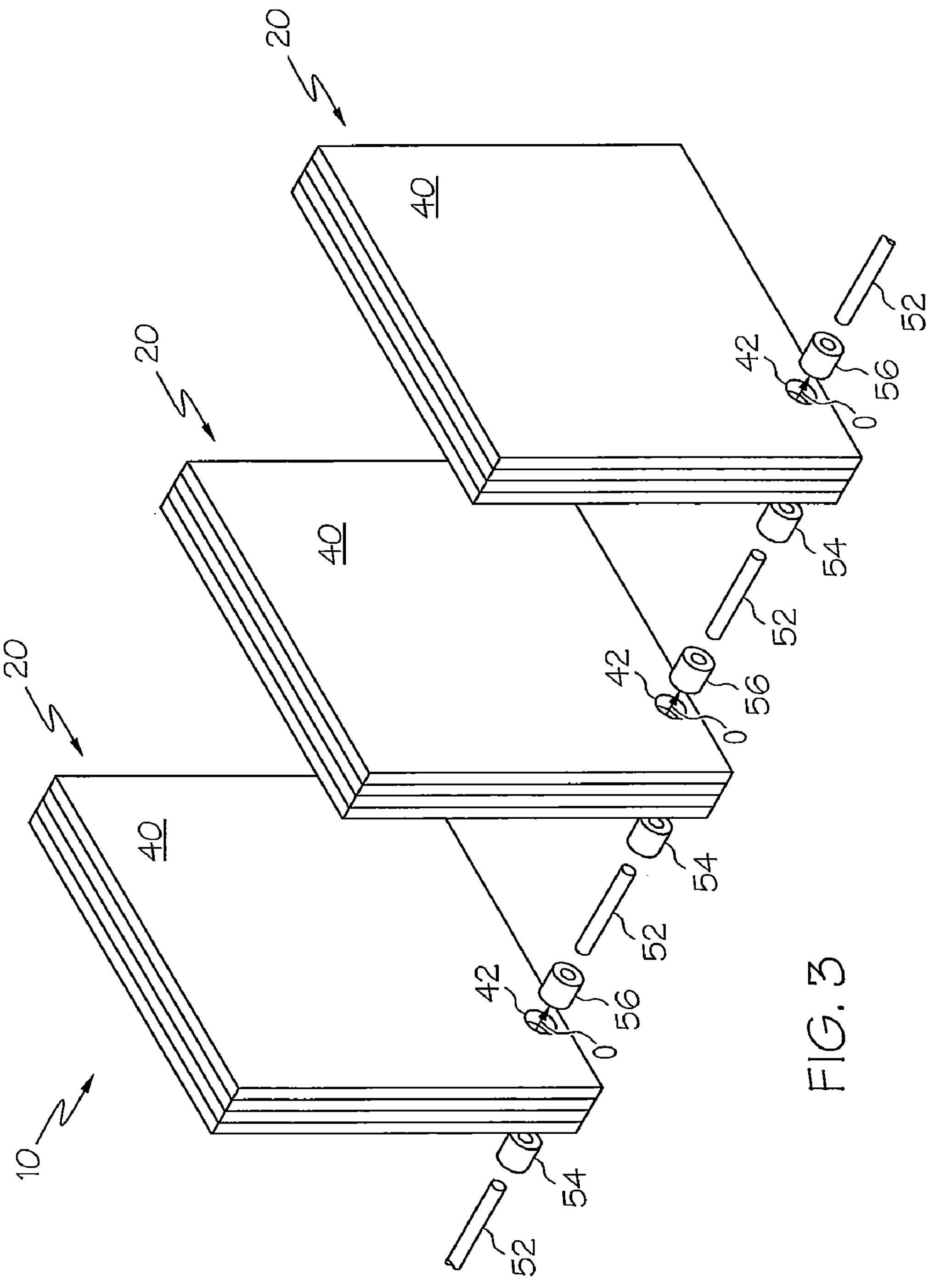
FIG. 3 is an exploded perspective view depicting the microfluidic assembly from the outlet side of the according to one or more embodiments of the present disclosure.
Figure 4:
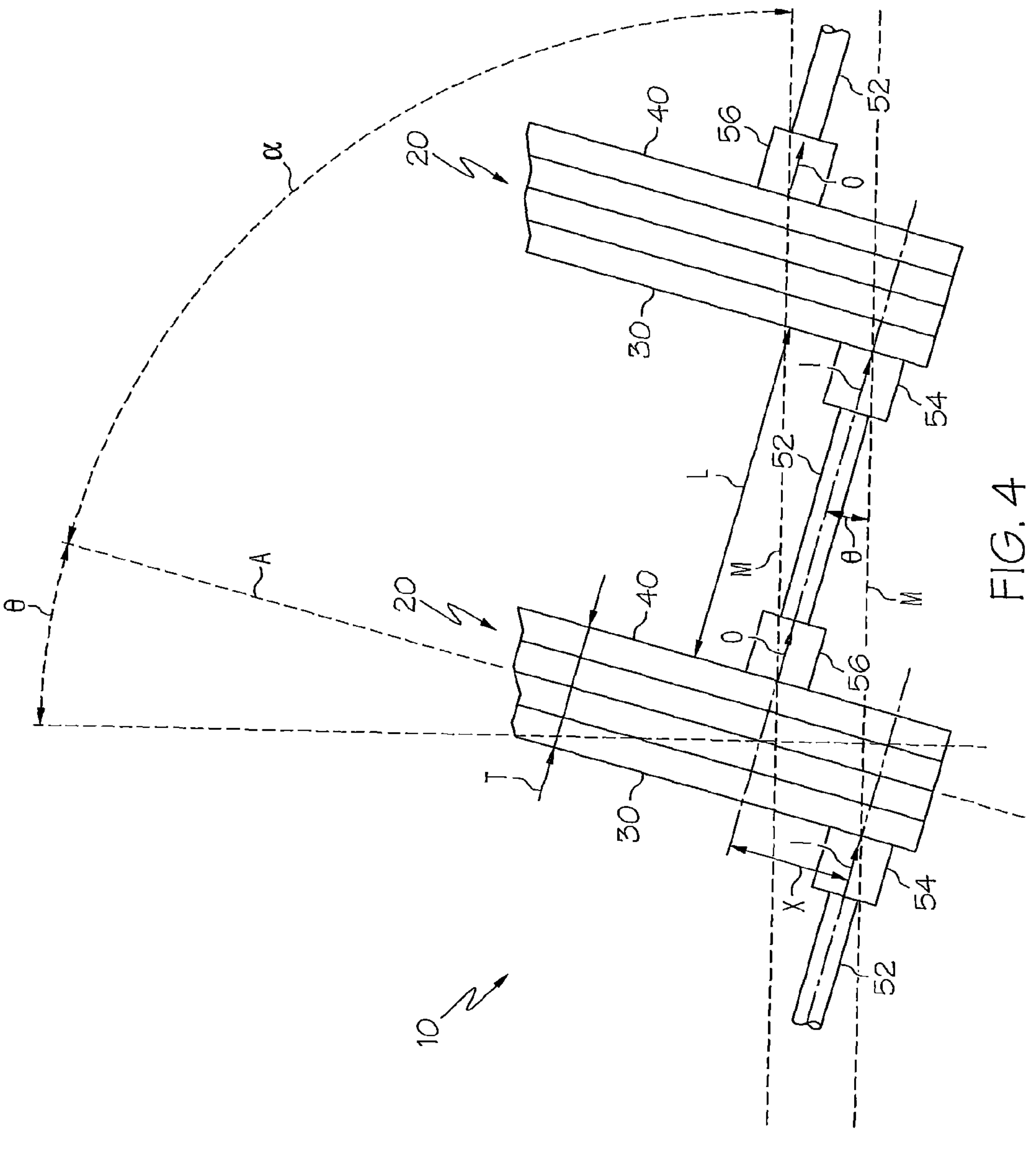
FIG. 4 is another top view of a microfluidic assembly according to one or more embodiments of the present disclosure.

Each microstructure 20 comprises at least one inlet port 32 disposed on an inlet side 30 of the microstructure 20 and at least one outlet port 42 disposed on an outlet side 40 of the microstructure 20. The outlet side 40 is opposite the inlet side 30 of the microstructure 20. As shown in FIGS. 1-3, the inlet port 32 defines an inlet flow path I. Similarly as shown in FIGS. 1, 3, and 4, the outlet port 42 defines an outlet flow path O. As described in detail below, the inlet flow path I and the outlet flow path O are not aligned along a common axis, and are offset by a distance X FIGS. 2 and 3 depict the inlet port 32 and the outlet port 42 as holes; however, other structures, for example, outward projections are also contemplated for the inlet port 32 and the outlet port 42.

As shown in FIGS. 1-3, the interconnecting fluid conduit 50 may connect an outlet port 42 of one microstructure 20 to an inlet port 32 of an adjacent microstructure 20. In one embodiment, the interconnecting fluid conduit 50 may be straight. While various components are contemplated, the interconnecting fluid conduit 50 may comprise a straight connector 54 coupled to the inlet port 32, a straight connector 56 coupled to the outlet port 42, and straight tubing 52 disposed between the inlet port connector 54 and the outlet port connector 56. Using a straight interconnecting fluid conduit 50 avoids costs associated with more complex connectors (e.g., connectors with angles or elbows) and minimizes pressure drop associated with these complex connectors. Moreover, the microfluidic assembly 10 further comprises securing devices (not shown) to couple the interconnecting fluid conduit 50 to the inlet port 32 and the outlet port 42. In one embodiment, the securing devices comprise clamps. The fixtures or clamps that secure the metal connectors to the microstructure can be independent for each inlet or outlet port, to achieve the better alignment of the connectors 54, 56 and the respective ports 32, 42.

Each microstructure 20 comprises an internal planar flow path that is defined by a plurality of internal mixing channels extending between the inlet port 32 and the outlet port 42 and is oriented along a microstructure offset axis A of the microstructure 20. The internal planar flow path is in fluid communication with the inlet port 32 and the outlet port 42. It is contemplated that the mixing channels may be curved, straight, or combinations thereof, depending on the desired residence time for the reaction. To reduce pressure drop, at the outlet port 42 of the microstructures 20, the outlet flow path O of each microstructure 20 can be configured to extend-from the internal planar flow path uni-directionally. Moreover, to reduce pressure at the inlet port 32 of the microstructures 20, the inlet flow path I of each microstructure can be configured to extend to the internal planar flow path uni-directionally.

Additionally as shown in FIG. 4, the microfluidic assembly 10 defines a microfluidic assembly axis M along which respective inlet ports 32 of adjacent microstructures 20 are oriented or alternatively along which respective outlet ports 42 of adjacent microstructures 20 are oriented. The internal planar flow path inside the microstructure 20 is oriented relative to the microfluidic assembly axis M at a nonorthogonal angle α i.e., an oblique or acute angle. Referring to FIGS. 1-3, the inlet port 32 may be disposed at a position closer to the edge of the inlet side 30 relative to the position of the outlet port 42 on the outlet side 40. This yields a configuration wherein the microstructures 20 are disposed at an acute nonorthogonal angle relative to the microfluidic assembly axis M. In an alternative embodiment, the outlet port 42 may be disposed at a position closer to the edge of the outlet side 40 relative to the position of the inlet port 32 on the inlet side 30. This yields a configuration wherein the microstructures are disposed at an oblique nonorthogonal angle relative to the microfluidic assembly axis M.

Referring to FIG. 4, the nonorthogonal angle is offset from orthogonal relative to the microfluidic assembly axis M via an angular offset 6. While various definitions for the angular offset are contemplated herein, the angular offset $\theta=\tan^{-1}(X/(L+T))$, wherein X is the distance between the inlet flow path I and the outlet flow path O along a projection parallel to a microstructure offset axis A, L is the distance between the outlet side 40 of one microstructure 20 and the inlet side 30 of an adjacent microstructure 20, and T is the distance between the inlet side 30 and the outlet side 40 of one microstructure 20. In one or more embodiments, the angular offset θ may be between about 1 and about 90°, or between about 10 and about 60°, or between about 15 to 45°. With the above definition of the angular offset θ, the microfluidic assembly may define defines a reactor length H, which is equal to $H=2(L+T)/\cos\theta$.

As would be familiar to one of ordinary skill in the art, the microstructure 20 may comprise various suitable materials. For example, the microstructure may comprise glass, or glass ceramic material, for example, a glass or glass ceramic material comprising silicon dioxide ($SiO_2$) and boric oxide ($B_2O_3$), a silica sheet or combinations thereof. One suitable commercial material is Vycor® produced by Corning Incorporated. The interconnecting fluid conduit 50 may also comprise various materials, for example, metal, polymeric, glass, ceramic, and glass-ceramic, or combinations thereof. The inlet port connector 54 and the outlet port connector 56 may also comprise metal, rigid polymeric materials, glass, ceramic, and glass-ceramic, or combinations thereof. In one exemplary embodiment, the inlet port connector 54 and the outlet port connector 56 comprises steel. Similarly, the straight tubing 52 comprises metal, rigid polymeric material, glass, ceramic, and glass-ceramic, or combinations thereof. In one embodiment, the straight tubing comprises perfluoroalkoxy plastic material. In another embodiment, the straight tubing comprises chemically-resistant steel. In yet another embodiment, the straight tubing comprises alumina.

The methods and/or devices disclosed herein are generally useful in performing any process that involves mixing, separation, extraction, crystallization, precipitation, or otherwise processing fluids or mixtures of fluids, including multiphase mixtures of fluids—and including fluids or mixtures of fluids including multiphase mixtures of fluids that also contain solids—within a microstructure. The processing may include a physical process, a chemical reaction defined as a process that results in the interconversion of organic, inorganic, or both organic and inorganic species, a biochemical process, or any other form of processing. The following non-limiting list of reactions may be performed with the disclosed methods and/or devices: oxidation; reduction; substitution; elimination; addition; ligand exchange; metal exchange; and ion exchange. More specifically, reactions of any of the following non-limiting list may be performed with the disclosed methods and/or devices: polymerisation; alkylation; dealkylation; nitration; peroxidation; sulfoxidation; epoxidation; ammoxidation; hydrogenation; dehydrogenation; organometallic reactions; precious metal chemistry/homogeneous catalyst reactions; carbonylation; thiocarbonylation; alkoxylation; halogenation; dehydrohalogenation; dehalogenation; hydroformylation; carboxylation; decarboxylation; amination; arylation; peptide coupling; aldol condensation; cyclocondensation; dehydrocyclization; esterification; amidation; heterocyclic synthesis; dehydration; alcoholysis; hydrolysis; ammonolysis; etherification; enzymatic synthesis; ketalization; saponification; isomerisation; quaternization; formylation; phase transfer reactions; silylations; nitrile synthesis; phosphorylation; ozonolysis; azide chemistry; metathesis; hydrosilylation; coupling reactions; and enzymatic reactions.

For the purposes of describing and defining the present invention it is noted that the term "approximately", "about", "substantially" or the like are utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. Moreover, although the term "at least" is utilized to define several components of the present invention, components which do not utilize this term are not limited to a single element.

To the extent that any meaning or definition of a term in this written document conflicts with any meaning or definition of the term in a document incorporated by reference, the meaning or definition assigned to the term in this written document shall govern.

Having described the claimed invention in detail and by reference to specific embodiments thereof, it will be apparent that modifications and variations are possible without departing from the scope defined in the appended claims. More specifically, although some aspects are identified herein as preferred or particularly advantageous, it is contemplated that the present claims are not necessarily limited to these preferred aspects.

What is claimed is:

1. A microfluidic assembly comprising at least two adjacent microstructures and a plurality of interconnecting fluid conduits, wherein:

each microstructure comprises at least one inlet port disposed on an inlet side of the microstructure and at least one outlet port disposed on an outlet side of the microstructure opposite the inlet side of the microstructure;

the inlet port defines an inlet flow path;

the outlet port defines an outlet flow path;

the inlet flow path and the outlet flow path are not aligned along a common axis;

respective ones of the interconnecting fluid conduits connect an outlet port of one microstructure to an inlet port of an adjacent microstructure;

each microstructure comprises an internal planar flow path in fluid communication with the inlet port and the outlet port;

the microfluidic assembly defines a microfluidic assembly axis along which respective inlet ports of adjacent microstructures are oriented or alternatively along which respective outlet ports of adjacent microstructures are oriented; and each microstructure is oriented relative to the microfluidic assembly axis at a nonorthogonal angle.

2. The microfluidic assembly of claim 1 wherein the nonorthogonal angle is defined as $\alpha$ and is offset from orthogonal relative to the microfluidic assembly axis M via an angular offset $\theta$, the angular offset $\theta=\tan^{-1}(X/(L+T))$, wherein X is the distance between the inlet flow path and the outlet flow path along a projection parallel to a microstructure offset axis A, L is the distance between the outlet side of one microstructure and the inlet side of the adjacent microstructure, and T is the distance between the inlet side and the outlet side of one microstructure.

3. The microfluidic assembly of claim 2 wherein the microfluidic assembly defines a reactor length H, which is equal to $H=2(L+T)/\cos\theta$.

4. The microfluidic assembly of claim 2 wherein the angular offset $\theta$ is between 15 to 45°.

5. The microfluidic assembly of claim 1 wherein the outlet flow path of each microstructure extends from the internal planar flow path uni-directionally.

6. The microfluidic assembly of claim 1 wherein the inlet flow path of each microstructure extends to the internal planar flow path uni-directionally.

7. The microfluidic assembly of claim 1 wherein each microstructure comprises a plurality of mixing channels extending between the inlet port and outlet port, wherein the plurality of mixing channels define the internal planar flow path.

8. The microfluidic assembly of claim 1 wherein the inlet port is disposed at a position closer to the edge of the inlet side relative to the position of the outlet port on the outlet side.

9. The microfluidic assembly of claim 1 wherein the outlet port is disposed at a position closer to the edge of the outlet side relative to the position of the inlet port on the inlet side.

10. The microfluidic assembly of claim 1 wherein the interconnecting fluid conduit is straight.

11. The microfluidic assembly of claim 10 wherein the straight conduit comprises straight tubing extending from the inlet port to the outlet port.

12. The microfluidic assembly of claim 10 further comprising securing devices to couple the interconnecting fluid conduits to the inlet and outlet ports.

13. The microfluidic assembly of claim 1 wherein the interconnecting fluid conduits comprise a straight connector coupled to the inlet port, a straight connector coupled to the outlet port, and straight tubing disposed between the inlet port connector and the outlet port connector.

14. The microfluidic assembly of claim 13 wherein the inlet port connector and the outlet port connector comprises metal, steel, or combinations thereof.

15. The microfluidic assembly of claim 13 wherein the straight tubing comprises rigid polymeric material.

16. The microfluidic assembly of claim 13 wherein the straight tubing comprises perfluoroalkoxy plastic material.

17. The microfluidic assembly of claim 13 wherein the straight tubing comprises a metal.

18. The microfluidic assembly of claim 13 wherein the straight tubing comprises one or more of glass, ceramic, and glass-ceramic.

19. The microfluidic assembly of claim 13 wherein the inlet port and outlet port comprises holes or outward projections.

* * * * *